(12) United States Patent
Themens et al.

(10) Patent No.: US 8,012,459 B2
(45) Date of Patent: Sep. 6, 2011

(54) FINE-TEXTURE COSMETIC COMPOSITION

(75) Inventors: Agnes Themens, Bourg la Reine (FR); Maitena Leuridan, Paris (FR)

(73) Assignee: L'Oreal, Paris (FR)

( * ) Notice: Subject to any disclaimer, the term of this patent is extended or adjusted under 35 U.S.C. 154(b) by 88 days.

(21) Appl. No.: 11/346,394

(22) Filed: Feb. 3, 2006

(65) Prior Publication Data

US 2006/0177401 A1    Aug. 10, 2006

Related U.S. Application Data

(60) Provisional application No. 60/661,939, filed on Mar. 16, 2005.

(30) Foreign Application Priority Data

Feb. 4, 2005    (FR) ...................... 05 50342

(51) Int. Cl.
  *A61Q 1/12*    (2006.01)
  *A61Q 1/02*    (2006.01)
  *A61K 9/14*    (2006.01)

(52) U.S. Cl. ............. 424/69; 424/401; 424/63; 424/489

(58) Field of Classification Search .................... 424/69, 424/401; 514/506
See application file for complete search history.

(56) References Cited

U.S. PATENT DOCUMENTS

| | | | |
|---|---|---|---|
| 4,980,157 A | 12/1990 | Mercado et al. | |
| 5,246,694 A | 9/1993 | Birthwistle | |
| 5,738,841 A | 4/1998 | Mellul et al. | |
| 5,766,611 A | 6/1998 | Shimono et al. | |
| 5,928,652 A | 7/1999 | Bodelin-LeComte | |
| 5,931,997 A | 8/1999 | Bäbler | |
| 6,344,205 B1 | 2/2002 | Grimm et al. | |
| 6,372,202 B1 | 4/2002 | Simon | |
| 6,428,795 B2 * | 8/2002 | Miura et al. | 424/401 |
| 2004/0197286 A1 | 10/2004 | Robert et al. | |

FOREIGN PATENT DOCUMENTS

| | | |
|---|---|---|
| EP | 0 723 776 A1 | 7/1996 |
| EP | 0 892 023 A1 | 1/1999 |
| EP | 1 044 677 A1 | 10/2000 |
| FR | 2 745 493 A1 | 9/1997 |
| FR | 2 854 063 A1 | 10/2004 |
| JP | A 61-85309 | 4/1986 |
| JP | A 61-257908 | 11/1986 |
| JP | A 4-270208 | 9/1992 |
| JP | A 9-241130 | 9/1997 |
| JP | A 10-218732 | 8/1998 |
| JP | A 10-259315 | 9/1998 |
| JP | A 11-106690 | 4/1999 |
| JP | A 2000-212042 | 8/2000 |
| JP | A 2000-336015 | 12/2000 |

OTHER PUBLICATIONS

Flick, E., Cosmetic Additives, 1991, Noyes Publications, p. 309, 311.*

Poucher's Perfumes, Cosmetics and Soaps, 2000, Kluwer Academic Publishers, (10th ed. by Hilda Butler), pp. 182-187.*

\* cited by examiner

*Primary Examiner* — Gina C Yu

(74) *Attorney, Agent, or Firm* — Oliff & Berridge, PLC

(57) ABSTRACT

The present invention relates to a pulverulent cosmetic composition, comprising, in a physiologically acceptable medium, an amount effective as binder of at least one short ester and of at least one silicone derivative, wherein: the mass content of short ester(s) is greater than the mass content of silicone derivative(s); and/or the said amount is less than 8% by weight relative to the total weight of the composition.

10 Claims, No Drawings

FINE-TEXTURE COSMETIC COMPOSITION

CROSS-REFERENCE TO RELATED APPLICATIONS

This non provisional application claims the benefit of French Application No. 05 50342 filed on Feb. 4, 2005 and U.S. Provisional Application No. 60/661,939 filed on Mar. 16, 2005.

BACKGROUND

The present invention relates to a pulverulent cosmetic composition for making up the skin, and also to a process that is useful for preparing it.

A large proportion of cosmetic compositions, and especially of makeup compositions such as makeup rouges, eyeshadows and foundations for the face, have a pulverulent appearance. They are mainly compositions conventionally termed "compact powders" or "loose powders", consisting essentially of a mixture of coloured or uncoloured powders and of a binder, generally a fatty binder, especially comprising oils. These powders are generally applied to the skin using an applicator, for instance a sponge, a powder-puff or a brush.

Besides an aesthetic effect in terms of makeup, the user generally expects, when using such products, firstly comfort of wear and of application, and secondly good staying power over time. The properties in terms of comfort of wear and of application are especially reflected by qualities such as softness, fluidity, ability to slide and to melt on the skin, and by a very fine and creamy texture. The properties in terms of staying power over time are reflected especially by the maintenance of good properties of obtaining staying power of the makeup over time. Now, for the reasons mentioned below, the reconciliation of these two aspects, comfort of wear and of application and staying power over time, in the same composition is not fully optimized.

Specifically, the aspect of fluidity and/or softness on application is generally associated with the nature and amount of the selected binder. A composition should contain an amount of binder sufficient to ensure a homogeneous appearance thereof, to give it good spreadability during application, to prevent the degradation of the makeup over time, and also, in the particular case of compact powders, to ensure good erodability thereof and to prevent their fragmentation, which may be caused especially by impacts. Now, in certain circumstances, the nature of the binder and this sufficient amount of binder may prove to be detrimental in terms of comfort of application and of wear.

SUMMARY

Consequently, there is at the present time a need for pulverulent cosmetic compositions, intended especially for making up the skin, which are fully satisfactory in terms of properties of comfort of application and of wear and of staying power. More particularly, there is a need for a binder with which compositions that are satisfactory in these terms can be obtained.

The object of the present invention is, precisely, to satisfy the needs mentioned above.

Consequently, according to one of its aspects, the invention relates to a pulverulent cosmetic composition, especially for making up the skin, characterized in that it comprises, in a physiologically acceptable medium, an amount effective as binder of at least one short ester and of at least one silicone derivative, the mass content of short ester(s) being greater than the mass content of silicone derivative(s).

According to another of its aspects, the invention relates to a pulverulent cosmetic composition, especially for making up the skin, characterized in that it comprises, in a physiologically acceptable medium, an amount effective as binder of at least one short ester and of at least one silicone derivative, the said amount being less than 8% by weight relative to the total weight of the composition.

According to another of its aspects, the invention also relates to a pulverulent cosmetic composition, especially for making up the skin, characterized in that it comprises, in a physiologically acceptable medium, at least:
  an amount effective as binder of at least one short ester, and
  at least 15% by weight of at least one spherical organic filler relative to the total weight of the composition.

According to another of its aspects, the invention relates to a compacted cosmetic composition comprising, in a physiologically acceptable medium, at least:
  one pulverulent phase,
  an amount effective as binder of at least one short ester,
  the said composition having, after decompacting, a granulometry D 50 expressed in terms of volume of less than 12 μm and a polydispersity of less than 2.

The inventors have also discovered that specific conditions of use of such a binder for the preparation of a pulverulent cosmetic composition can improve the expected qualities thereof, especially in calorimetric terms.

According to another of its aspects, the invention relates to a pulverulent cosmetic composition comprising as binder at least one short ester, characterized in that it is obtained by micronization, especially with a jet of air, of all of its components, the said short ester being added, after the said micronization step with mechanical stirring, in a proportion of at least 90% by weight relative to its total weight in the said composition.

According to one variant of the invention, the binder may comprise, besides a short ester in accordance with the invention, at least one silicone derivative as defined below.

According to another aspect, the invention relates to a process for preparing a pulverulent powder composed of at least one pulverulent filler and of an amount effective as binder of at least one short ester, characterized in that it comprises at least the steps consisting in:
  micronizing with a jet of air all of the components of the said pulverulent filler in the presence, where appropriate, of less than 10% by weight of the said short ester relative to its total weight in the said composition, and
  mixing the micronized pulverulent filler obtained after the preceding step with at least 90% by weight of the said short ester relative to its total weight in the said composition.

According to one embodiment variant, the short ester is integrally incorporated after the micronization step. In this case, the binder that may be introduced during the micronization step may be the silicone derivative used together with the short ester as binder in the composition.

In point of fact, the introduction of binder during the micronization step is mainly to be preferred for reasons of safety.

Such a process is especially advantageous since it enables optimization of the colour saturation effect afforded by the dyestuffs in the composition.

The process according to the invention also has the advantage of giving the composition a smaller and more uniform granulometry. This granulometry is reflected for the user by improved qualities of feel of the composition, in particular an improvement in the softness and the creamy sensation of the composition when it is touched and applied. The compacting of the composition and the appearance of the compact case are also improved and the composition thus obtained is more uniform and has a finer texture.

According to another of its aspects, a subject of the invention is a process for making up a keratin material, especially the skin, comprising the application to the surface to be made up of a composition in accordance with the invention.

As stated previously, the invention is based especially on the use, as binder, of at least one short ester.

DETAILED DESCRIPTION OF EMBODIMENTS

For the purposes of the invention, the term "amount effective as binder" denotes the necessary and sufficient amount of short ester(s), where appropriate combined with at least one silicone derivative to ensure, in the case of compact powders, the cohesion of all of the particles, and, in the case of loose powders, a uniform, fluidized appearance that does not lend itself to the formation of particle aggregates.

The composition may contain from 0.5% to 100% of binder and, according to one aspect of the invention, may more particularly contain from 1% to 50%, especially from 2% to 15%, in particular from 3% to 11% and more particularly from 4% to 9%, for example from 4.5% to 8% or even from 5% to 7% by weight of binder, relative to the total weight of the composition.

When the composition comprises, as sole compound, one or more short ester(s), the abovementioned percentages apply to the amount of short ester(s).

I-Short Ester

For the purposes of the invention, the term "short ester" denotes esters of monocarboxylic acids with monoalcohols and polyalcohols.

The esters in accordance with the invention may be monoesters, diesters or polyesters and are more particularly monoesters.

Advantageously, the said ester corresponds to formula (I) below:

$$R_1\text{—CO—O—}R_2 \quad (I)$$

where $R_1$ represents a linear or branched alkyl radical of 1 to 40 carbon atoms and preferably of 7 to 19 carbon atoms, optionally comprising one or more ethylenic double bonds, and optionally substituted.

$R_2$ represents a linear or branched alkyl radical of 1 to 40 carbon atoms, preferably of 3 to 30 carbon atoms and better still of 3 to 20 carbon atoms, optionally comprising one or more ethylenic double bonds, and optionally substituted.

The term "optionally substituted" means that $R_1$ and/or $R_2$ can bear one or more substituents chosen, for example, from groups comprising one or more hetero atoms chosen from O, N and S, such as amino, amine, alkoxy and hydroxyl.

Preferably, the total number of carbon atoms of $R_1+R_2$ is greater than or equal to 9.

More particularly the groups $R_1$ and $R_2$ are such that the corresponding ester is non-volatile.

$R_1$ may represent the residue of a linear or, preferably, branched fatty acid, preferably a higher fatty acid, containing from 1 to 40 and even better from 7 to 19 carbon atoms, and $R_2$ may represent a linear or, preferably, branched hydrocarbon-based chain containing from 1 to 40, preferably from 3 to 30 and even better from 3 to 20 carbon atoms. Once again, preferably the number of carbon atoms of $R_1+R_2$ is greater than or equal to 9.

Examples of groups $R_1$ are those derived from fatty acids chosen from the group consisting of acetic acid, propionic acid, butyric acid, caproic acid, caprylic acid, pelargonic acid, capric acid, undecanoic acid, lauric acid, myristic acid, palmitic acid, stearic acid, isostearic acid, arachidic acid, behenic acid, oleic acid, linolenic acid, linoleic acid, elaeostearic acid, arachidonic acid and erucic acid, and mixtures thereof.

Examples of esters that can be used in the binder of the compositions of the invention include purcellin oil (cetostearyl octanoate), isodecyl neopentanoate isononyl isononanoate, isopropyl myristate, 2-ethylhexyl palmitate, 2-octyldodecyl stearate, 2-octyldodecyl erucate, isostearyl isostearate, and heptanoates, octanoates, decanoates or ricinoleates of alcohols or polyalcohols, for example of fatty alcohols.

More particularly, the short esters according to the invention are of $C_9$ to $C_{40}$, especially of $C_{10}$ to $C_{25}$ and more particularly of $C_{12}$ to $C_{20}$.

Advantageously, the esters are chosen from the compounds of formula (I) above, in which $R_1$ represents an unsubstituted linear or branched alkyl group of 1 to 40 carbon atoms and preferably of 7 to 19 carbon atoms, optionally comprising one or more ethylenic double bonds, and $R_2$ represents an unsubstituted linear or branched alkyl group of 1 to 40 carbon atoms, preferably of 3 to 30 carbon atoms and even better of 3 to 20 carbon atoms, optionally comprising one or more ethylenic double bonds.

Preferably, $R_1$ is an unsubstituted branched alkyl group of 4 to 14 carbon atoms and preferably of 8 to 10 carbon atoms, and $R_2$ is an unsubstituted branched alkyl group of 5 to 15 carbon atoms and preferably of 9 to 11 carbon atoms. The short ester will preferably be chosen from the following compounds:

isodecyl neopentanoate,
isononyl isononanoate,
cetostearyl octanoate,
isopropyl myristate,
2-ethylhexyl palmitate,
2-octyldodecyl stearate,
2-octyldodecyl erucate,
isostearyl isostearate, and mixtures thereof.

Isodecyl neopentanoate is found to be most particularly advantageous for obtaining compositions that have very satisfactory visual and tactile qualities.

As stated above, the inventors have found that the use of at least one short ester as binder proves to be particularly advantageous for ensuring a low granulometry for pulverulent compositions. In the particular case of compact powders, this granulometry is advantageously preserved even after decompacting.

Thus, in the particular case of a compact powder, this composition may have, after decompacting, a granulometry (D50) ranging from 6 to 12 µm and especially ranging from 7 to 10.5 µm, with (D50) corresponding to the particle size defined such that 50% of the volume of the particles have a size less than (D50).

The polydispersity may be less than 2, especially less than 1.8 and in particular less than 1.6.

The term "polydispersity" means the value of the ratio $$\frac{(D90)-(D10)}{(D50)},$$

with (D90) corresponding to the size of particle defined such that 90% of the volume of the particles have a size less than (D90), (D10) corresponding to the size of particle defined such that 10% of the volume of the particles have a size less than (D10) and (D50) as defined above.

The mean volume size may be assessed with a laser granulometer, for example the Mastersizer 2000 machine from Malvern or the BI90+ machine from Broockhaven Instrument Corporation.

This granulometry measurement may especially be performed according to the following protocol:

The compacted product is broken up using a spatula over a screen with a mesh size of 250μ. The powder aggregates obtained are then screened. The whole is recovered and the granulometric characteristics are determined using the Malvern granulometer.

As stated previously, the short ester is present in the composition in an amount sufficient to provide a binder function therein. For obvious reasons, this amount can vary significantly according to the nature of the short ester.

By way of non-limiting illustration, the binder of the composition may advantageously comprise from 2% to 100% by weight, preferably from 50% to 100% by weight and more preferably from 50% to 75% by weight of short ester(s).

II—Silicone Derivative

According to one particular aspect of the invention, the binder combines at least one short ester with at least one silicone derivative.

Advantageously, the short ester(s)/silicone derivative(s) weight ratio may be greater than or equal to 1, especially greater than 1.5 and even more particularly greater than 2.

The term "silicone derivative" includes all compounds containing silicone and belonging, respectively, to the family of silicone oils, to the family of silicone resins, to the family of silicone waxes and to the family of silicone gums.

In a first variant of the invention, the binder may combine at least one short ester with at least two silicone derivatives belonging to the same family, for example two silicone oils.

In another variant of the invention, the binder may combine at least one short ester with at least two silicone derivatives belonging to two different families, for example a silicone oil and a silicone resin.

1) Silicone Oil

According to one variant of the invention, the binder comprises, besides at least one short ester, at least one silicone oil.

The silicone oil may be chosen from linear or cyclic volatile silicone oils, such as linear or cyclic polydimethylsiloxanes (PDMS) containing from 3 to 7 silicon atoms.

Examples of such oils that may be mentioned include the compounds mentioned in Table 1 below.

TABLE 1

| Compound | Flash point (° C.) | Viscosity (cSt) |
|---|---|---|
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane (L4) | 63 | 1.7 |
| KF 96 A from Shin Etsu PDMS (polydimethylsiloxane) | 94 | 6 |
| DC 200 (1.5 cSt) from Dow Corning | 56 | 1.5 |
| PDMS DC 200 (2 cSt) from Dow Corning | 87 | 2 |
| PDMS DC 200 (5 cSt) from Dow Corning | 134 | 5 |
| PDMS DC 200 (3 cSt) from Dow Corning | 102 | 3 |

The non-volatile silicone oils may be polydimethylsiloxanes, polyalkylmethylsiloxanes, dimethicone copolyols, alkylmethicone copolyols, cetyl dimethicone, silicones containing alkylglyceryl ether groups, silicones containing amine side groups and dilauroyltrimethylolpropane siloxysilicate. The alkyl groups of these oils especially contain from 2 to 24 carbon atoms.

The non-volatile silicone oils that may be used in the binder of the invention, which contains at least one short ester, may be in particular linear, non-volatile polydimethylsiloxanes (PDMS) that are liquid at room temperature; polydimethylsiloxanes comprising alkyl, alkoxy or phenyl groups, which are pendent and/or at the end of a silicone chain, these groups each containing from 2 to 24 carbon atoms; phenyl silicones, for instance phenyl trimethicones, phenyl dimethicones, phenyl trimethylsiloxy diphenylsiloxanes, diphenyl dimethicones, diphenyl methyldiphenyl trisiloxanes, 2-phenylethyl trimethylsiloxysilicates, fluorosilicones containing group(s) that is (are) pendent or at the end of a chain containing from 1 to 12 carbon atoms, all or some of the hydrogen atoms of which are substituted with fluorine atoms, and dimethiconols, and mixtures thereof.

For the purposes of the invention, the volatile oils have at room temperature (25° C.) and atmospheric pressure (760 mmHg) a vapour pressure ranging from 0.02 mmHg to 300 mmHg (2.66 Pa to 40 000 Pa) and better still ranging from 0.1 to 90 mmHg (13 Pa to 12 000 Pa). The corresponding non-volatile oils then have a vapour pressure of less than 0.02 mmHg (2.66 Pa).

The silicone oils have a viscosity advantageously chosen in the range from 5 to 800 000 cSt, preferably from 10 to 500 000 cSt and better still from 10 to 5000 cSt at 25° C.

In other words, the volatile silicone oil(s) may be chosen, for example, from the group consisting of the compounds of Table 1, heptamethyloctyltrisiloxane, dodecamethylpentasiloxane and polymethylcetyldimethylsiloxane, and mixtures thereof.

The volatile silicone oil may also be chosen from the group of fluorosilicone oils, such as silicones containing alkyl and perfluoroalkyl groups, silicone containing oxyethylene/oxypropylene (OE/OP) side groups and perfluoro groups, silicones containing perfluoro or polyfluoro side groups and glycerolated side groups, and perfluoroalkylmethylphenylsiloxanes, these oils having a vapour pressure of greater than or equal to 0.02 mmHg.

According to one aspect of the invention, the binder advantageously contains from 0.5% to 98%, preferably from 1% to 50% by weight, more preferably from 10% to 40% by weight and better still from 20% to 30% by weight of silicone oil.

Polydimethylsiloxanes, which allow the desired characteristics for the composition to be obtained, are most particularly suitable as silicone oils.

In one particularly advantageous embodiment, the binder comprises from 50% to 80% of short ester(s) and from 20% to 50% of silicone oil(s).

For example, a binder based on isodecyl neopentanoate with polydimethylsiloxane proves to be most particularly advantageous.

2) Silicone Resins

According to one variant of the invention, the binder comprises, besides at least one short ester, at least one silicone derivative including at least one silicone resin.

The silicone resins that may be used in the context of the invention are generally soluble or swellable in silicone oils. These resins are crosslinked polyorgano-siloxane polymers.

The nomenclature for silicone resins is known as "MDTQ", the resin being described as a function of the various siloxane monomer units it comprises, each of the letters "MDTQ" characterizing a type of unit.

The letter M represents the monofunctional unit of formula $(CH_3)_3SiO_{1/2}$, the silicon atom being linked to only one oxygen atom in the polymer comprising this unit.

The letter D denotes a difunctional unit $(CH_3)_2SiO_{2/2}$ in which the silicon atom is linked to two oxygen atoms.

The letter T represents a trifunctional unit of formula $(CH_3)SiO_{3/2}$ in which the silicon atom is linked to three oxygen atoms.

In the units M, D and T defined above, at least one of the methyl groups may be substituted with a group R other than a methyl group, such as a hydrocarbon-based radical (especially alkyl) containing from 2 to 10 carbon atoms or a phenyl group, or alternatively a hydroxyl group.

Finally, the letter Q means a tetrafunctional unit $SiO_{4/2}$ in which the silicon atom is linked to four hydrogen atoms, which are themselves linked to the polymer residue.

Various resins with different properties may be obtained from these various units, the properties of these polymers varying as a function of the type of monomers (or units), the type and number of substituted radicals, the length of the polymer chain, the degree of branching and the size of the pendent chains.

Examples of these silicone resins that may be mentioned include:

siloxysilicates, which may be trimethylsiloxysilicates of formula (II)

$$[(CH_3)_3-Si-O]_x-(SiO_{4/2})_y \qquad (II)$$

(units MQ) in which x and y are integers ranging from 50 to 80, polysilsesquioxanes of formula $(CH_3SiO_{3/2})_x$ (units T) in which x is greater than 100 and at least one of the methyl radicals of which may be substituted with a group R as defined above, the polymethylsilsesquioxanes, which are polysilsesquioxanes in which none of the methyl radicals is substituted with another group. Such polymethylsilsesquioxanes are described in document U.S. Pat. No. 5,246,694, the content of which is incorporated by reference.

As examples of commercially available polymethylsilsesquioxane resins, mention may be made of those sold:

by the company Wacker under the reference Resin MK, such as Belsil PMS MK: polymer comprising $CH_3SiO_{3/2}$ repeating units (units T), which may also comprise up to 1% by weight of $(CH_3)_2SiO_{2/2}$ units (units D) and having an average molecular weight of about 10 000, by the company Shin-Etsu under the references KR-220L, which are composed of units T of formula $CH_3SiO_{3/2}$ and contain Si—OH (silanol) end groups, under the reference KR-242A, which comprise 98% of units T and 2% of dimethyl units D and contain Si—OH end groups, or under the reference KR-251, comprising 88% of units T and 12% of dimethyl units D and contain Si—OH end groups.

Siloxysilicate resins that may be mentioned include trimethylsiloxysilicate resins (TMS) optionally in the form of powders. Such resins are sold under the reference SR1000 by the company General Electric or under the reference TMS 803 by the company Wacker. Mention may also be made of trimethylsiloxysilicate resins sold in a solvent such as cyclomethicone, sold under the name "KF-7312J" by the company Shin-Etsu or "DC 749" and "DC 593" by the company Dow Corning.

Among the silicone resins, trimethyl siloxysilicate is particularly advantageous in the context of the invention.

In one particularly advantageous embodiment, the binder comprises between 50% and 80% by mass of short esters, between 20% and 50% of a silicone oil and between 0 and 30% of a silicone resin.

In another embodiment in accordance with the invention, the binder comprises between 60% and 99.95% of short ester and from 0.05% to 40% of a silicone resin.

For example, a binder combining isodecyl neopentanoate, polydimethylsiloxane and trimethyl siloxysilicate is most particularly suitable for the invention.

3) Silicone Waxes

According to one variant of the invention, the binder comprises, besides at least one short ester, at least one silicone derivative including at least one silicone wax.

The silicone waxes that may be used in the fatty binder of the present invention are substituted polysiloxanes that are solid or liquid at room temperature. They are preferably fluid or solid with a low melting point. They are especially substituted linear polysiloxanes consisting essentially (apart from the end groups) of units of formulae III and IV, in the respective molar proportions m and n:

$$\left[ \begin{array}{c} R \\ | \\ Si-O \\ | \\ R \end{array} \right]_m \quad \text{and} \qquad (III)$$

$$\left[ \begin{array}{c} R' \\ | \\ Si-O \\ | \\ R \end{array} \right]_n \qquad (IV)$$

in which each substituent R is a lower alkyl group (containing 1 to 6 carbons), each R' independently represents an optionally unsaturated alkyl (linear or branched) containing 6-30 carbon atoms, or a group —X—R", each X independently represents:

—O—,

—$(CH_2)_a$—O—CO—,

—$(CH_2)_b$—CO—O—, a and b independently represent numbers possibly ranging from 0 to 6, and each R" independently represents an optionally unsaturated alkyl group containing 6 to 30 carbon atoms, m is a number possibly ranging from 0 to 400 and in particular from 0 to 100, n is a number possibly ranging from 1 to 200 and in particular from 1 to 100, the sum (m+n) being less than 400 and in particular less than or equal to 100.

These silicone waxes are known or may be prepared according to known methods. Among the commercial silicone waxes of this type that may especially be mentioned are those sold under the names Abil Wax 9800®, 9801® or 9810® (Goldschmidt), KF910® and KF7002® (Shin-Etsu) or 176-1118-3® and 176-11481® (General Electric).

Among these silicone waxes, polymethylcetyldimethylsiloxane is particularly suitable in the context of the invention.

The silicone waxes that may be used may also be chosen from the compounds of formula (V):

$$R_1-Si(CH_3)_2-O-[Si(R)_2-O-]_z-Si(CH_3)_2-R_2 \qquad (V)$$

in which:

R is defined as above, $R_1$ represents an alkyl group containing from 1 to 30 carbon atoms, an alkoxy group containing from 6 to 30 carbon atoms or a group of formula

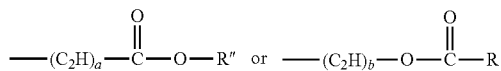

$R_2$ represents an alkyl group of 6 to 30 carbon atoms, an alkoxy group containing from 6 to 30 carbon atoms or a group of formula:

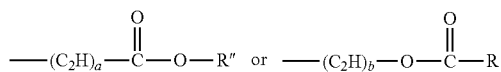

a and b representing a number from 0 to 6,

R" being an alkyl containing from 6 to 30 carbon atoms, and z is an number possibly ranging from 1 to 100.

Among the silicone waxes of formula (V), which are known products or which may be prepared according to known methods, mention will be made especially of the following commercial products: Abil Wax 2428', 2434® and 2440® (Goldschmidt), or VP 1622® and VP 1621® (Wacker).

In one particularly advantageous embodiment, the binder comprises from 50% to 80% by weight of short ester(s), from 10% to 50% of silicone oil(s), from 0 to 20% of silicone resin(s) and from 0 to 20% of silicone wax(es).

In another embodiment in accordance with the invention, the binder comprises from 60% to 99.95% of short ester(s) and from 0.05% to 40% of silicone wax(es). For example, a binder combining isodecyl neopentanoate, polydimethylsiloxane, trimethyl siloxysilicate and polymethylcetyldimethylsiloxane is most particularly suitable for the invention.

4) Silicone Gums

According to one variant of the invention, the binder comprises, besides at least one short ester, at least one silicone derivative including at least one silicone gum.

The silicone gums that may be used in accordance with the invention are polysiloxanes of high molecular masses, which may range, for example, from 200 000 to 1 000 000. They are used alone or as a mixture in a solvent. This solvent may be chosen especially from polydimethylsiloxane (PDMS) oils and polyphenylmethylsiloxane (PPMS) oils. They are also known and marketed products or may be prepared according to known methods. Mention may be made more particularly of the following silicone gums: polydimethylsiloxane/methylvinylsiloxane, polydimethylsiloxane/diphenylsiloxane, poly-dimethylsiloxane/phenylmethylsiloxane and polydimethyl-siloxane/diphenylsiloxane/methylvinylsiloxane.

Among the commercial silicone gums, mention may be made of those sold under the names SE30 (General Electric, TP232 (Union Carbide), Q2-1403 (Dow Corning) or the Viscasil series (General Electric).

III—Pulverulent Phase

The pulverulent phase generally present in the composition according to the invention comprises at least one spherical or lamellar mineral or organic filler, generally combined with at least one mineral dyestuff, especially of pigment type.

The compositions according to the invention may contain from 0.5% to 99.5% by weight of pulverulent phase, and, according to one aspect of the invention, may more particularly contain from 75% to 98% of pulverulent phase, especially from 85% to 97%, in particular from 90% to 96% or even from 93% to 95% by weight of pulverulent filler.

1. Fillers

The fillers may be mineral or organic. The fillers may be particles of any form, especially platelet-shaped, spherical or oblong, irrespective of their crystallographic form (for example lamellar, cubic, hexagonal, orthorhombic, etc.).

Among the fillers that may be used in the compositions according to the invention, mention may be made especially of talc, natural or synthetic mica, silica, kaolin, polyamide (Nylon®) powder, poly-β-alanine powder and polyethylene powder, tetrafluoroethylene polymer (Teflon®) powders, lauroyllysine, starch, boron nitride and acrylic acid polymer powders, silicone resin microbeads (for example Tospearls® from Toshiba), bismuth oxychlorides, precipitated calcium carbonate, magnesium carbonate, magnesium hydrogen carbonate and hydroxyapatite, hollow silica microspheres (such as "Silica Beads SB 700/HA®" or "Silica Beads SB 700®" from the company Maprecos, and the "Sunspheres H-33®" and "Sunspheres H-51®" products from the company Asahi Glass), acrylic polymer microspheres (such as those made of crosslinked acrylate copolymer "Polytrap 6603 Adsorber®" from the company RP Scherrer and those made of polymethyl methacrylate "Micropearl M 100®" from the company SEPPIC), polyurethane powders (such as the powder of the copolymer of hexamethylene diisocyanate and of trimethylol hexyl lactone sold under the name "Plastic Powder D-400®" by the company Toshiki), glass or ceramic microcapsules, metal soaps derived from organic carboxylic acids containing from 8 to 22 carbon atoms and especially from 12 to 18 carbon atoms, for example zinc stearate, magnesium stearate, lithium stearate, zinc laurate or magnesium myristate, methyl acrylate or methacrylate polymer or copolymer microcapsules, or vinylidene chloride and acrylonitrile copolymer microcapsules, for instance "Expancel®" from the company Expancel;

elastomeric crosslinked organopolysiloxane powders, such as those sold under the name "Trefil Powder E-506C" by the company Dow Corning, powders of elastomeric crosslinked organopolysiloxane coated with silicone resin, such as those sold under the names "KSP-100", "KSP-101", "KSP-102", "KSP-103", "KSP-104" and "KSP-105" by the company Shin-Etsu, and mixtures thereof.

According to one embodiment of the invention, the composition contains at least one spherical organic filler chosen especially from those mentioned above. They may especially be polyamide (Nylon®) powders (Orgasol® from Atochem), polyethylene powders, tetrafluoroethylene polymer (Teflon®) powders, starch, polymer microspheres such as those of polyvinylidene chloride/acrylonitrile, for instance Expancel® (Nobel Industrie), acrylic acid copolymers (Polytrap® from the company Dow Corning), silicone resin microbeads (for example Tospearls® from Toshiba) and elastomeric organopolysiloxanes.

2. Mineral or Organic Dyestuff

The pulverulent phase of the composition according to the invention may advantageously contain at least one pulverulent dyestuff that may be chosen from the pigments and nacres usually used in cosmetic and/or dermatological compositions.

The pigments may be white or coloured, mineral and/or organic, and coated or uncoated. Among the mineral pigments that may especially be mentioned are titanium dioxide, optionally surface-treated, zirconium oxide or cerium oxide, and also iron oxide or chromium oxide, manganese violet, ultramarine blue, chromium hydrate and ferric blue. Among the organic pigments that may especially be mentioned are carbon black, pigments of D & C type and lakes based on cochineal carmine or on barium, strontium, calcium or aluminium.

The nacres may be chosen from white nacreous pigments such as mica coated with titanium or with bismuth oxychloride, coloured nacreous pigments such as titanium mica with iron oxides, titanium mica with, especially, ferric blue or chromium oxide, titanium mica with an organic pigment of the abovementioned type and nacreous pigments based on bismuth oxychloride.

The pulverulent dyestuff may generally be present in the composition in a content ranging from 0.5% to 35% by weight, especially from 1% to 20% by weight and in particular from 3% to 15% by weight relative to the total weight of the composition.

IV—Physiologically Acceptable Medium

The term "physiologically acceptable medium" denotes a non-toxic medium that may be applied to keratin materials and especially to human skin. The physiologically acceptable medium is generally suited to the nature of the skin onto which the composition is to be applied, and also to the form in which the composition is intended to be packaged, especially in the form of a compact or loose powder at atmospheric pressure.

Thus, the compositions according to the invention may be formulated in a form of loose or compact powder type.

Besides the abovementioned compounds, the composition according to the invention may comprise non-silicone derivatives such as non-silicone oils and/or non-silicone solid fatty substances.

It is understood that the presence of these compounds in the composition according to the invention should not be prejudicial to the presentation of the expected qualities in terms of comfort of application and aesthetic effect afforded moreover by the presence of the short ester, optionally combined with a silicone derivative.

1. Non-Silicone Oil

The volatile non-silicone oils may be chosen from the group of hydrocarbon-based oils and volatile esters and ethers such as volatile hydrocarbons, for instance isododecane, isohexadecane and $C_8$-$C_{16}$ isoparaffins.

The volatile non-silicone oil may also be chosen from fluoro oils such as perfluoropolyethers, perfluoroalkanes, for instance perfluorodecalin, perfluoroadamantanes, perfluoroalkyl phosphate monoesters, diesters and triesters, and fluoro ester oils.

As examples of volatile non-silicone oils that may be used in the composition of the invention, mention may be of the compounds in Table 2 below.

TABLE 2

| Compound | Flash point (° C.) |
| --- | --- |
| Isododecane | 43 |
| Isohexadecane | 102 |
| Propylene glycol n-butyl ether | 60 |

TABLE 2-continued

| Compound | Flash point (° C.) |
| --- | --- |
| Ethyl 3-ethoxypropionate | 58 |
| Propylene glycol methyl ether acetate | 46 |
| Isopar L (C11-C13 isoparaffin) | 62 |
| Isopar H (C11-C12 isoparaffin) | 56 |

The composition may also contain at least one polar oil such as:

hydrocarbon-based plant oils with a high triglyceride content, consisting of fatty acid esters of glycerol, the fatty acids of which may have varied chain lengths, these chains possibly being linear or branched, and saturated or unsaturated; these oils are especially wheatgerm oil, corn oil, sunflower oil, shea oil, castor oil, sweet almond oil, macadamia oil, apricot oil, soybean oil, rapeseed oil, cottonseed oil, alfalfa oil, poppyseed oil, pumpkin oil, sesame seed oil, marrow oil, avocado oil, hazelnut oil, grapeseed oil, blackcurrant seed oil, evening primrose oil, millet oil, barley oil, quinoa oil, olive oil, rye oil, safflower oil, candlenut oil, passion flower oil or musk rose oil; or alternatively caprylic/capric acid triglycerides, for instance those sold by the company Stearines Dubois or those sold under the names Miglyol 810, 812 and 818 by the company Dynamit Nobel, synthetic ethers containing from 10 to 40 carbon atoms, $C_8$ to $C_{26}$ fatty alcohols, for instance oleyl alcohol or octyldodecanol, fatty acids, for instance oleic acid, linoleic acid or linolenic acid, and mixtures thereof.

It may also contain one or more apolar oils such as linear or branched, volatile or non-volatile hydrocarbons or fluorocarbons of synthetic or mineral origin, for instance volatile liquid paraffins (such as isoparaffins and isododecane) or non-volatile liquid paraffins and derivatives thereof, petroleum jelly, polydecenes, hydrogenated polyisobutene such as Parleam, and squalane, and mixtures thereof.

2. Non-Silicone Solid Fatty Substances

The compositions according to the invention may also comprise at least one non-silicone solid fatty substance, which may be chosen from waxes and pasty compounds.

For the purposes of the present invention, the term "wax" means a lipophilic compound that is solid at room temperature (25° C.), which undergoes a reversible solid/liquid change of state, and which has a melting point of greater than or equal to 30° C., which may be up to 120° C.

By bringing the wax to the liquid state (melting), it is possible to make it miscible with the oils that may be present and to form a microscopically homogeneous mixture, but on reducing the temperature of the mixture to room temperature, recrystallization of the wax in the oils of the mixture takes place. The melting point of the wax may be measured using a differential scanning calorimeter (DSC), for example the calorimeter sold under the name DSC 30 by the company Mettler.

The wax may also have a hardness ranging from 0.05 MPa to 15 MPa and preferably ranging from 6 MPa to 15 MPa. The hardness is determined by measuring the compressive force, measured at 20° C. using the texturometer sold under the name TA-TX2i by the company Rheo, equipped with a stainless-steel cylinder 2 mm in diameter travelling at a measuring speed of 0.1 mm/s, and penetrating into the wax to a penetration depth of 0.3 mm.

The waxes may be hydrocarbon-based waxes, fluoro waxes and/or silicone waxes, and may be of plant, mineral, animal and/or synthetic origin. In particular, the waxes have a melting point of greater than 30° C. and better still greater than 45° C.

As waxes that may be used in the first composition of the invention, mention may be made of beeswax, carnauba wax or candelilla wax, paraffin, microcrystalline waxes, ceresin or ozokerite; synthetic waxes, for instance polyethylene waxes or Fischer-Tropsch waxes.

The compositions may also contain a micronized wax, also known as a microwax.

As microwaxes that may be used in the compositions according to the invention, mention may be made of carnauba microwaxes, such as the product sold under the name "Micro-Care 350®" by the company Micro Powders, synthetic microwaxes, such as that product sold under the name "MicroEase 114S®" by the company Micro Powders, microwaxes consisting of a mixture of carnauba wax and polyethylene wax, such as the products sold under the names "Micro Care 300®" and "310®" by the company Micro Powders, microwaxes consisting of a mixture of carnauba wax and of synthetic wax, such as the product sold under the name "Micro Care 325®" by the company Micro Powders, polyethylene microwaxes, such as the products sold under the names "Micropoly 200®", "220®", "220L®" and "250S®" by the company Micro Powders, and polytetrafluoroethylene microwaxes such as the products sold under the names "Microslip 519®" and "519 L®" by the company Micro Powders.

Among the microwaxes mentioned above, some of them, for instance carnauba microwax, the synthetic microwax "MicroEase 114S®" or the microwax consisting of a mixture of carnauba wax and of synthetic wax "MicroCare 325®", have a starting melting point of greater than or equal to 45° C.

These compositions may also contain at least one pasty compound, which may be chosen advantageously from:
- lanolin and its derivatives
- polymeric or non-polymeric fluoro compounds
- vinyl polymers, especially:
  - olefin homopolymers
  - olefin copolymers
  - hydrogenated diene homopolymers and copolymers
  - linear or branched oligomers, homopolymers or copolymers of alkyl (meth)acrylates preferably containing a C8-C30 alkyl group
  - oligomers, homopolymers and copolymers of vinyl esters containing C8-C30 alkyl groups
  - oligomers, homopolymers and copolymers of vinyl ethers containing C8-C30 alkyl groups
- liposoluble polyethers resulting from the polyetherification between one or more C2-C100 and preferably C2-C50 diols
- esters, and
- mixtures thereof.

Among the esters, the following are especially preferred:
- esters of a glycerol oligomer, especially diglycerol esters, in particular condensates of adipic acid and of glycerol, for which some of the hydroxyl groups of the glycerols have reacted with a mixture of fatty acids such as stearic acid, capric acid, stearic acid and isostearic acid, and 12-hydroxystearic acid, especially such as those sold under the brand name Softisan 649 by the company Sasol,
- the arachidyl propionate sold under the brand name Waxenol 801 by Alzo,
- phytosterol esters,
- fatty acid triglycerides and derivatives thereof,
- pentaerythritol esters,
- and mixtures thereof.

Among the pasty compounds of plant origin that will preferably be chosen is a mixture of oxyethylenated (5 OE) oxypropylenated (5 OP) soybean sterols and of pentaerythritol, sold under the reference Lanolide by the company Vevy.

The composition may also comprise other ingredients (adjuvants) usually used in cosmetics, for instance water-soluble or liposoluble dyes, preserving agents, cosmetic active agents, moisturizers, UV-screening agents, thickeners, water, surfactants, gelling agents and/or fragrances.

Needless to say, a person skilled in the art will take care to select the optional adjuvant(s) added to the composition according to the invention such that the advantageous properties intrinsically associated with the composition in accordance with the invention are not, or are not substantially, adversely affected by the envisaged addition.

The composition according to the invention may especially be in the form of a makeup product of compact or loose powder type, in particular a makeup rouge, an eyeshadow, a face powder, a foundation, a concealer product or a body makeup product, or alternatively in the form of a facial care product or a bodycare product.

The examples that follow illustrate the invention. In these examples, the amounts of the various ingredients are given as parts by weight.

Examples 1 to 4

Preparation of a foundation comprising, in mass percentages:

| | Example 1 | Example 2 | Example 3 | Example 4 |
| --- | --- | --- | --- | --- |
| Methyl, ethyl, propyl, butyl, isobutyl p-hydroxybenzoates/2-phenoxyethanol mixture (Phenonip from the company Nipa (Clariant) | 0.60% | 0.60% | 0.60% | 0.60% |
| Titanium dioxide | 0.00% | 2.00% | 2.00% | 2.00% |
| Yellow iron oxide (CI: 77492) | 1.90% | 1.90% | 2.20% | 1.90% |
| Brown, yellow iron oxides (75/25) (CI: 77491 + 77492) | 0.80% | 0.80% | 1.00% | 0.80% |
| Black iron oxide (CI: 77499) | 0.35% | 0.35% | 0.80% | 0.35% |
| Nylon 12 powder (Orgasol 2002 Exd Nat Cos 204 from the company Arkema) | 20.00% | 20.00% | 20.00% | 20.00% |
| Polydimethylsiloxane (viscosity: 10 cSt) (Fluid DC 200 10 CS from the company Dow Corning) | 1.23% | 1.23% | 1.23% | 1.23% |
| Polydimethylsiloxane/trimethylsiloxysilicate mixture (Dow Corning 593 fluid from the company Dow Corning) | 0.39% | 0.39% | 0.39% | 0.39% |
| Polymethylcetyldimethylsiloxane (MW: 900 - viscosity: 15/25 cSt) (Abil Wax 9801 from the company Goldschmidt) | 0.24% | 0.24% | 0.24% | 0.24% |

-continued

|  | Example 1 | Example 2 | Example 3 | Example 4 |
|---|---|---|---|---|
| Mica (CI: 77019) | 20.00% | 20.00% | 30.00% | 30.00% |
| Triisocetyl citrate (Citmol 316 from the company Bernel Chemical (Alzo) | 0.10% | 0.10% | 0.10% | 0.10% |
| Bismuth oxychloride (CI: 77163) | 10.00% | 10.00% | 0.00% | 10.00% |
| Talc | 36.35% | 34.35% | 33.40% | 34.35% |
| Magnesium stearate | 4.00% | 4.00% | 4.00% | 4.00% |
| Deodorized isodecyl neopentanoate (Dub VCI 10 from the company Sterinerie Dubois) | 4.05% | 4.05% | 4.05% | 2.05% |
| Ethylhexyl methoxycinnamate | 0.00% | 0.00% | 0.00% | 2.00% |

Although the present invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A pulverulent cosmetic composition, comprising:
at least one spherical organic filler; and
an effective amount of a binder in a physiologically acceptable medium, the binder comprising:
at least one short ester; and
at least one silicone derivative, wherein:
the at least one short ester is a monoester selected from the group consisting of isodecyl neopentanoate, isononyl isononanoate, 2-ethylhexyl palmitate, 2-octyldodecyl stearate, 2-octyldodecyl erucate and isostearyl isostearate;
the spherical organic filler is selected from the group consisting of polyamide powders, polyethylene powders, tetrafluoroethylene polymer powders, starch, microspheres of polyvinylidene chloride/acrylonitrile, microspheres of acrylic acid copolymers, silicon resin microbeads, and elastomeric organopolysiloxanes;
the spherical organic filler is present in an amount of at least 15% by weight relative to a total weight of the composition;
the mass content of the at least one short ester is greater than the mass content of the silicone derivative; and
the effective amount of the binder is less than 8% by weight relative to a total weight of the composition, wherein the spherical organic filler is present in an amount equal to or greater than 20% by weight relative to the total weight of the composition.

2. The composition according to claim 1, wherein the silicone derivative comprises at least one member selected from the group consisting of silicone oils, silicone resins, silicone waxes and silicone gums.

3. The composition according to claim 2, wherein the silicone derivative comprises at least two members selected from the group consisting of silicone oils, silicone resins, silicone waxes and silicone gums.

4. The composition according to claim 2, wherein:
the silicone derivative comprises at least a first silicone derivative and a second silicone derivative;
each of the first silicone derivative and the second silicone derivative comprises the same member selected from the group consisting of silicone oils, silicone resins, silicone waxes and silicone gums; and
the first silicone derivative is different from the second silicone derivative.

5. The composition according to claim 1, wherein the silicone derivative comprises at least one silicone oil selected from the group consisting of dimethicone, polydimethylsiloxanes, polyphenylmethylsiloxanes, octamethylcyclotetrasiloxane, decamethylcyclopentasiloxane, dodecylmethylcyclohexasiloxane, hepamethylhexyltrisiloxane, heptamethyloctyltrisiloxane, hexamethyldisiloxane, octamethyltrisiloxane, decamethyltetrasiloxane, dodecamethylpentasiloxane, phenyl trimethicones, phenyl dimethicones, phenyl trimethylsiloxy diphenylsiloxanes, diphenyl dimethicones, diphenyl methyldiphenyl trisiloxanes and 2-phenylethyl trimethyl siloxysilicates.

6. The composition according to claim 1, wherein the silicone derivative comprises trimethyl siloxysilicate resin.

7. The composition according to claim 1, wherein the silicone derivative comprises polydimethylcetyldimethylsiloxane wax.

8. The composition according to claim 1, wherein the spherical organic filler is a polyamide.

9. A process for making up a keratin material, comprising applying the composition according to claim 1 to a surface to be made up.

10. A composition for making up the skin comprising the pulverulent cosmetic composition according to claim 1.

* * * * *